United States Patent
Maev et al.

(10) Patent No.: US 10,330,782 B2
(45) Date of Patent: Jun. 25, 2019

(54) ULTRASONIC ADAPTIVE BEAMFORMING METHOD AND ITS APPLICATION FOR TRANSCRANIAL IMAGING

(71) Applicant: Tessonics Corporation, Birmingham, MI (US)

(72) Inventors: Roman G. Maev, Windsor (CA); Kiyanoosh Shapoori, Toronto (CA); Eugene V. Malyarenko, Troy, MI (US)

(73) Assignee: Tessonics Corporation, Birmingham, MI (US)

( * ) Notice: Subject to any disclaimer, the term of this patent is extended or adjusted under 35 U.S.C. 154(b) by 763 days.

(21) Appl. No.: 14/935,999

(22) Filed: Nov. 9, 2015

(65) Prior Publication Data

US 2016/0187473 A1 Jun. 30, 2016

Related U.S. Application Data (60) Provisional application No. 62/076,857, filed on Nov. 7, 2014.

(51) Int. Cl.
*G01S 7/52* (2006.01)
*A61B 8/08* (2006.01)
(Continued)

(52) U.S. Cl.
CPC ........ *G01S 7/52049* (2013.01); *A61B 8/0808* (2013.01); *A61B 8/0816* (2013.01);
(Continued)

(58) Field of Classification Search
None
See application file for complete search history.

(56) References Cited

U.S. PATENT DOCUMENTS

| 4,852,577 A | 8/1989 | Smith et al. |
| 5,052,394 A | 10/1991 | Carpenter et al. |

(Continued)

FOREIGN PATENT DOCUMENTS

| EP | 2515762 A1 | 10/2012 |
| WO | 2010042146 A2 | 4/2010 |

OTHER PUBLICATIONS

Shapoori et al., "Transmission mode adaptive beamforming for planar phased arrays and its application to 3D ultrasonic transcranial imaging," Mar. 29, 2013, Proceedings of SPIE, vol. 8675, pp. 1-6.*

(Continued)

*Primary Examiner* — James M Kish (74) *Attorney, Agent, or Firm* — Carlson, Gaskey & Olds, P.C.

(57) ABSTRACT

A method for ultrasonic imaging a volume behind a barrier includes placing an array of elements of a probe adjacent the barrier. The local thickness and the sound speed in the barrier are estimated. A plurality of sub-apertures are defined in the array of elements, each sub-aperture defined by a different sub-set of adjacent ones of the array of elements. Ultrasonic waveforms are collected from each of the sub-apertures by focusing each sub-aperture approximately at the inner surface of the barrier. The ultrasonic waveforms through each of the sub-aperture elements are combined to generate a combined A-mode waveform. A profile of an inner surface of the barrier adjacent the probe is extracted based upon the combined A-mode waveforms. A correction is calculated based upon the profile of the inner surface. The volume behind the barrier is scanned using beamforming based upon the correction to generate an image of the volume.

14 Claims, 6 Drawing Sheets

(51) Int. Cl.
*A61B 8/00* (2006.01)
*G01S 15/89* (2006.01)
*A61B 8/14* (2006.01)

(52) U.S. Cl.
CPC ............ *A61B 8/0858* (2013.01); *A61B 8/145* (2013.01); *A61B 8/4444* (2013.01); *A61B 8/4488* (2013.01); *A61B 8/4494* (2013.01); *A61B 8/5207* (2013.01); *A61B 8/5223* (2013.01); *A61B 8/5269* (2013.01); *G01S 15/8927* (2013.01)

(56) References Cited

U.S. PATENT DOCUMENTS

| | | | |
|---|---|---|---|
| 5,331,964 | A | 7/1994 | Trahey et al. |
| 5,673,699 | A | 10/1997 | Trahey et al. |
| 6,612,988 | B2 | 9/2003 | Maor et al. |
| 6,705,994 | B2 | 3/2004 | Vortman et al. |
| 6,770,031 | B2 | 8/2004 | Hynymen et al. |
| 7,175,599 | B2 | 2/2007 | Hynymen et al. |
| 7,300,414 | B1 | 11/2007 | Holland et al. |
| 7,344,509 | B2 | 3/2008 | Hynynen et al. |
| 8,088,067 | B2 | 1/2012 | Vortman et al. |
| 2005/0160817 | A1 | 7/2005 | Clement et al. |
| 2007/0167805 | A1 | 7/2007 | Clement |
| 2012/0165670 | A1 | 6/2012 | Shi et al. |

OTHER PUBLICATIONS

Wydra et al., "Development of a practical ultrasonic approach for simultaneous measurement of the thickness and the sound speed in human skull bones: a laboratory phantom study," Jan. 31, 2013, Institute of Physics and Engineering in Medicine, 58, pp. 1083-1102.*
Malyarenko et al., "Ultrasonic Lamb wave diffraction tomography," Jun. 2001, Ultrasonics, vol. 39, pp. 269-281.*
Wang et al., "Transcranial ultrasound imaging with speed of sound-based phase correction: a numerical study," Sep. 9, 2009, Institute of Physics and Engineering in Medicine, 58, pp. 6663-6681.*
Vasudevan, "Ultrasonic Digital Beamformation: A Comparative Study," Sep. 14, 1998, McGill University, pp. 1-85.*
Time Reversal of Ultrasonic Fields—Part I: Basic Principles, Mathias Fink, IEEE Transactions on Ultrasonics, Ferroelectrics, and Frequency Control, vol. 39, No. 5, Sep. 1992.
Time Reversal of Ultrasonic Fields—Part II: Experimental Results, Wu et al., IEEE Transactions on Ultrasonics, Ferroelectrics, and Frequency Control, vol. 39, No. 5, Sep. 1992.
Time Reversal of Ultrasonic Fields—Part III: Theory of the Closed Time-Reversal Cavity, Cassereau et al., IEEE Transactions on Ultrasonics, Ferroelectrics, and Frequency Control, vol. 39, No. 5, Sep. 1992.
Time Reversal and Phase Conjugation with Acoustic Waves: Industrial and Medical Applications, Mathias Fink, 2005 Conference on Lasers & Electro-Optics (CLEO).
Phase-Aberration Correction Using Signals From Point Reflectors and Diffuse Scatterers: Basic Principles, Flax et al., IEEE Transactions on Ultrasonics, Ferroelectrics, and Frequency Control, vol. 35, No. 6, Nov. 1988.
Phase-Aberration Correction Using Signals From Point Reflectors and Diffuse Scatterers: Measurements, O'Donnell et al., IEEE Transactions on Ultrasonics, Ferroelectrics, and Frequency Control, vol. 35, No. 6, Nov. 1988.
Phase Aberration Measurements in Medical Ultrasound: Human Studies, O'Donnell et al., Trasonic Imaging 10, 1-11 (1988).
Phase-Aberration Correction with a 3-D Ultrasound Scanner: Feasibility Study, Ivancevich et al., IEEE Transactions on Ultrasonics, Ferroelectrics, and Frequency Control, vol. 53, No. 8, Aug. 2006.
Experimental Results with a Real-Time Adaptive Ultrasonic Imaging System for Viewing through Distorting Media, Trahey et al., IEEE Transactions on Ultrasonics, Ferroelectrics, and Frequency Control, vol. 37, No. 5, Sep. 1990.
Phase aberration correction in medical ultrasound using speckle brightness as a quality factor, Nock et al., Department of Biomedical Engineering, Duke University, Jan. 1989.
Adaptive ultrasonic array inhomogeneous layer, Hirama et al., The Graduate School of Nagatsuta, Tokyo Institute of Technology, Jul. 1981.
Imaging through an inhomogeneous layer by least-mean-square error fitting, Hirama et al., The Graduate School of Nagatsuta, Tokyo Institute of Technology, Oct. 1983.
Direct estimation of aberrating delays in pulse-echo imaging systems, Daniel Rachlin, Information Systems Laboratory, Department of Electrical Engineering, Stanford University, Jan. 1990.
Phase Aberration Correction Using Near-Field Signal Redundancy—Part I: Principles, Yue Li, IEEE Transactions on Ultrasonics, Ferroelectrics, and Frequency Control, vol. 44, No. 2, Mar. 1997.
Phase Aberration Correction Using Near-Field Signal Redundancy—Part II: Li et al., IEEE Transactions on Ultrasonics, Ferroelectrics, and Frequency Control, vol. 44, No. 2, Mar. 1997.
The Influences of Ambiguity Phase Aberration Profiles on Focusing Quality in the Very Near Field—Part II: Dynamic Range Focusing on Reception, Yue Li, IEEE Transactions on Ultrasonics, Ferroelectrics, and Frequency Control, vol. 49, No. 1, Jan. 2002.
Implementation of the Near-Field Signal Redundancy Phase-Aberration Correction Algorithm on Two-Dimensional Arrays, Li et al., IEEE Transactions on Ultrasonics, Ferroelectrics, and Frequency Control, vol. 54, No. 1, Jan. 2007.

* cited by examiner

ULTRASONIC ADAPTIVE BEAMFORMING METHOD AND ITS APPLICATION FOR TRANSCRANIAL IMAGING

BACKGROUND

Noninvasive ultrasonic imaging of static foreign objects through the human skull or any other highly scattering multilayered solid structure (acoustical barrier) is difficult. The acoustical barrier possesses different acoustic impedance than the interfacing media, so implementation of conventional phased array imaging techniques results in significant image quality degradation. Where the intact human skull is the barrier, the foreign objects could be pieces of bone fragments, pieces of shrapnel, air bubbles, blood clots with high reflectivity, etc., which have higher/lower acoustic impedance than the surrounding brain tissue. The objects can be lodged at different depths, ranging from immediately under the skull up to several centimeters deep in the brain tissue. The thickness of the skull varies unevenly around the skull, which further causes image distortion.

SUMMARY

The present method resolves accurate location of static objects and structures hidden under the human skull or behind any other highly scattering multilayered solid structure (acoustical barrier). The acoustical barrier should possess different acoustic impedance than the interfacing media and thickness greater than or comparable to the wavelength of transmitted acoustical field. The images are obtained noninvasively through the skull/barrier by a single, small-footprint, handheld matrix or linear ultrasonic phased array probe.

The sound speed in the skull bone or barrier material and the profile of the skull/barrier segment under the probe are measured as follows:
1. If allowed by the driving electronics and by the probe, switch to a higher-frequency excitation signal to improve the in-depth resolution of the skull profile.
2. Simultaneously estimate the local thickness and the sound speed in the skull bone or barrier using a known algorithm, such as an iterative focusing algorithm or similar.
3. Using a small sub-aperture comprised of several adjacent elements of the matrix/linear probe, approximately focused at depth of about one skull/barrier thickness under the probe's surface (on the inner surface of the skull/barrier), collect an A-mode waveform containing the reflections from the front and inner surfaces of the skull/barrier. Such waveform is obtained via standard beamforming and summation of RF signals over the sub-aperture elements, and then optionally enhanced by averaging over multiple acquisitions.
4. Collect a sequence of said acoustic A-mode waveforms over the grid of points on the inner surface of the skull/barrier by moving the said small aperture over the probe in a raster scanning (or any other desired) manner. The points in said grid may be distributed unevenly, e.g. sparser where the surface is smooth and denser elsewhere.
5. Extract the profile of the skull/barrier layer under the matrix probe by a cross-correlation technique or any other time delay estimation algorithm.
6. Smooth and oversample the obtained skull/barrier profile by means of interpolation or any other appropriate algorithm.
7. If higher frequency was used at the step 1, switch back to the lower-frequency excitation signal to optimize the trade-off between skull penetration and spatial resolution.

Alternatively, the skull/barrier profile and acoustical properties can be obtained not with the same phased array probe as the one used for beamforming and imaging purposes. For example, these properties can be obtained from a separate acoustic measurement with a different (e.g. higher-frequency) probe, from X-Ray Computed Tomography, Magnetic Resonance Imaging etc.

As another alternative, the local thickness and the sound speed in the skull bone or barrier can be estimated separately (i.e. not simultaneously), using available tools.

By accurately tracing refracted acoustic rays between individual array elements and the given intended focal point through the bone/barrier and the media behind it, the system calculates time delays for the elements of transmit and receive apertures that would allow to achieve accurate single-point focusing in both transmission (active) and reception (passive) modes.

The system and method implement beamforming algorithms both in transmission and reception modes using timing sequences calculated above that are dynamically adapted to the measured local properties and geometry of the skull/barrier to correct for the phase aberration and refraction effects. The algorithms implement spatial apodization to produce optimized directivity pattern of the acoustic field, i.e. enhanced main lobe and suppressed side lobes, in both transmission and reflection modes.

The system and method combine the results of adaptive active and passive focusing at a prescribed number of points distributed in the imaged volume to generate an image of said volume with objects and structures showing at their correct locations.

The system and method may represent the results as interactive 3D maps in one of the common data storage formats (e.g. DICOM), which can be output to an image viewer.

The tracing of the refracted acoustic rays between individual array elements and the intended focal point through the bone/barrier and the media behind it may be accomplished by solving the Helmholtz wave propagation equation numerically in each medium with appropriate boundary conditions. For this, the algorithm searches through the boundary points and picks the one at which all constraints, including the Fermat's principle and boundary conditions, are satisfied. Therefore the ultrasound transmitted from the array element under consideration to the desired focal point in the brain will pass through this point on the skull-brain interface. For optimum results, more points may be interpolated in between the original grid points on highly undulating areas of the inner boundary. On the other hand, when the thickness profile has a smooth variation, some boundary points may be skipped. The above process may then be repeated for all the active array elements to find all the refracted paths.

The active and passive beamforming algorithms are not limited to those used in the preferred embodiment, namely, those using particular spatial and temporal apodization and frequency modulation to minimize the side lobes.

DETAILED DESCRIPTION OF A PREFERRED EMBODIMENT

Figure 1:
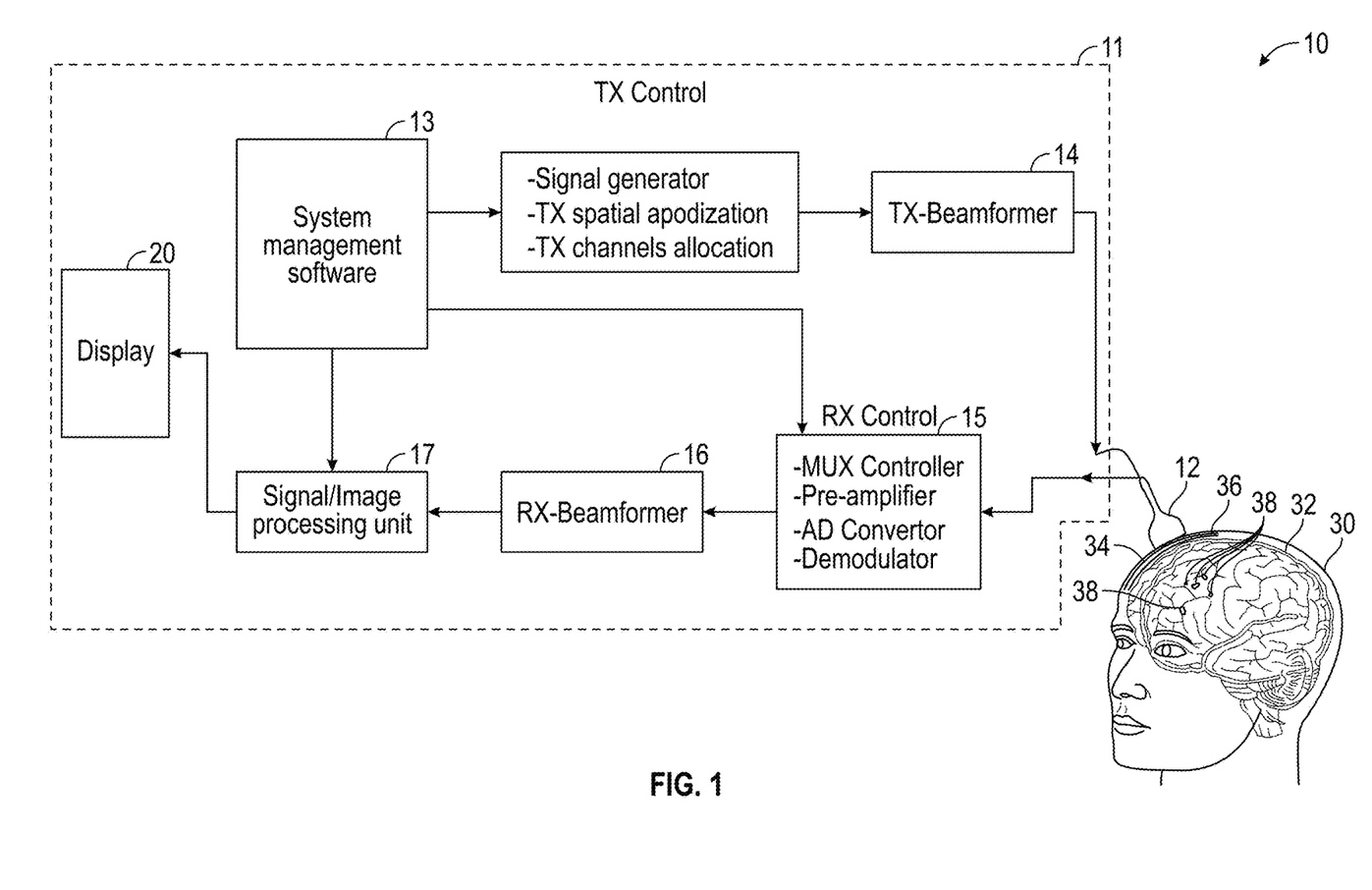
FIG. 1 shows an imaging system according to one embodiment of the present invention.

An imaging system 10 according to one embodiment of the present invention is shown schematically in FIG. 1. The imaging system 10 generally includes an ultrasonic phased array probe 12, such as a single, small-footprint, handheld matrix or linear ultrasonic phased array probe. The probe 12 is connected to a phased array controller 11 capable of performing on-the-flight adaptive time delay correction and other functions required by the algorithm. The phased array controller 11 includes management software running on a controller 13 (with processor, memory, etc), which governs the system's operation in both transmission (TX) and reception (RX) modes. In transmission, the adjustable parameters include the frequency, amplitude, and shape of the excitation signal, the arrangement of elements in the transmit aperture, and the spatial apodization over the transmit aperture. The active TX beamformer 14 applies both standard and adapted-to-the-barrier focal rules to the elements of the transmit aperture of the probe 12 to correct for the barrier-induced phase aberration of transmitted signals. In reception, the received echo signals pass through RX control 15, including an optional multiplexer, pre-amplifier, AD converter receiving the amplified signal, and demodulator. The digitized echo signals are modulated and saved to memory. The passive RX beamformer 16 then adjusts the individual delays of the echo signals for all elements of the receive aperture of the probe 12 to perform passive focusing and to correct for phase aberration due to the barrier. Signal and image processing routines are applied to the beamformed signals by signal/image processing unit 17 to enhance image quality, mainly in terms of resolution and contrast, prior to displaying the final sonogram. The phased array controller is in turn connected to a computer having at least one processor communicating with storage (such as electronic, magnetic, optical or other storage). Typical user interface hardware may be provided, such as a display 20, user input devices, etc. The computer carries high-level instructions to the phased array controller, receives the data from it, runs data post processing, visualization, and manipulation software, as well as controls the storage of the raw and processed data.

The probe 12 is shown adjacent the head of a patient 30 for imaging the patient's brain 32. Between the probe 12 and the brain 32 is skin 34 and skull 36. The system 10 illustrated in FIG. 1 can be used, for example, to detect, locate and/or image foreign objects 38 through the skull 36 by combining the transmission and reception ultrasonic modes, as explained below.

The system 10 performs a noninvasive ultrasonic adaptive beamforming method for imaging of static foreign objects 38 through the human skull 36 or any other highly scattering multilayered solid structure (acoustical barrier). The acoustical barrier should possess different acoustic impedance than the interfacing media. In presence of such barrier, implementation of conventional phased array imaging techniques results in significant image quality degradation. In case of the intact human skull 36 as the barrier, the foreign objects 38 could be pieces of bone fragments, pieces of shrapnel, air bubbles, blood clots with high reflectivity, etc., which have higher/lower acoustic impedance than the surrounding brain tissue 32. The objects 38 can be lodged at different depths, ranging from immediately under the skull 36 up to several centimeters deep in the brain tissue 32. The method uses an ultrasonic phased array 12 contacting the skull 36 either directly or through an intermediate layer (e.g. human head skin 34). An ultrasonic coupling agent can be used to optimize acoustic contact between the array and the skull 36 (or skin 34).

The adaptive beamforming method is based on the knowledge of the geometry and acoustical properties of the barrier (e.g. skull 36) segment in contact with the phased array 12. In one embodiment, the characteristics of the barrier (mainly longitudinal sound speed and thickness profile) are determined from the preliminary reflection-mode acoustic measurements. Such measurements are conducted prior to the main beamforming steps and may be done according to the techniques described in A. Wydra, E. Malyarenko, et al., "Development of a practical ultrasonic approach for simultaneous measurement of the thickness and the sound speed in human skull bones: a laboratory phantom study," *Phys. Med. Biol.*, vol. 58, no. 4, pp. 1083-102, February 2013, which is hereby incorporated by reference in its entirety. The measurements may be implemented via the same phased array 12 that is further used in the imaging process. Alternatively, these characteristics can be also obtained from other measurement modalities, including X-Ray CT images, independent ultrasonic measurements, literature data, or any other suitable means.

The adaptive beamforming method includes two separate modes, transmission (TX) and reception (RX), the merging of which results in obtaining a non-distorted image of the targeted objects 38. Each of the two modes includes a set of consecutive single-point adaptive focusing steps. Transmission adaptive focusing has an active nature while reception adaptive focusing is performed passively. The term adaptive focusing means adaptation of the phased array 12 timing pattern to the properties of the underlying barrier segment in order to refocus/redirect the acoustic beam to intended focal coordinates. To achieve accurate focusing, the new timing pattern should account for acoustic impedance mismatch at the barrier surfaces as well as attenuation in the propagation media. The corrected timing patterns are calculated in both transmission and reception modes and applied to the elements of the array together with proper spatial apodization rules. The final stage includes post-processing of the received signals and image reconstruction of the targeted objects showing their correct positions. Below, the above steps are explained in detail.

1. Extraction of the Skull/Barrier Profile

Figure 2:
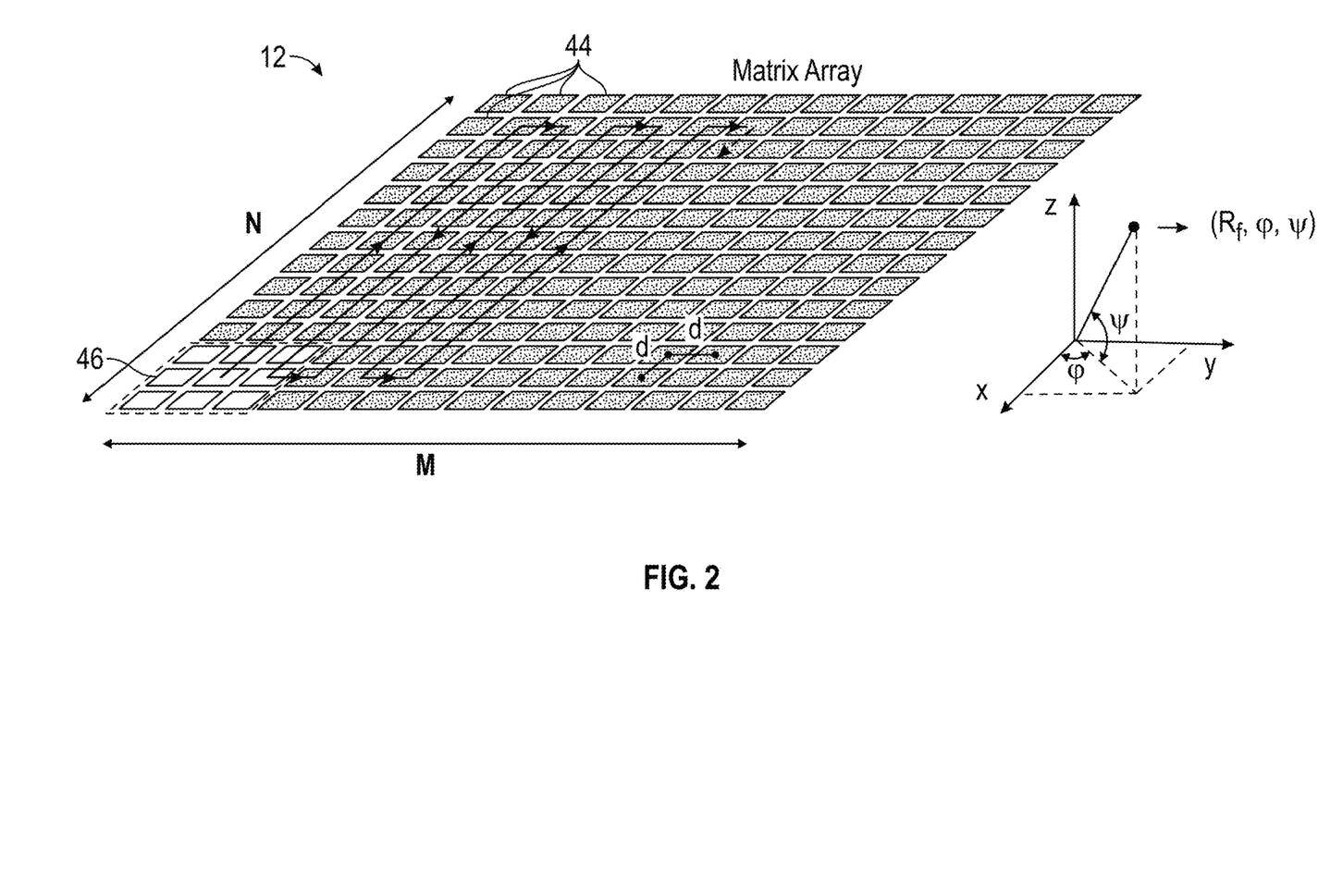
FIG. 2 shows an arrangement of the elements and their scanning path used for the profile extraction via the matrix probe.
Figure 3:
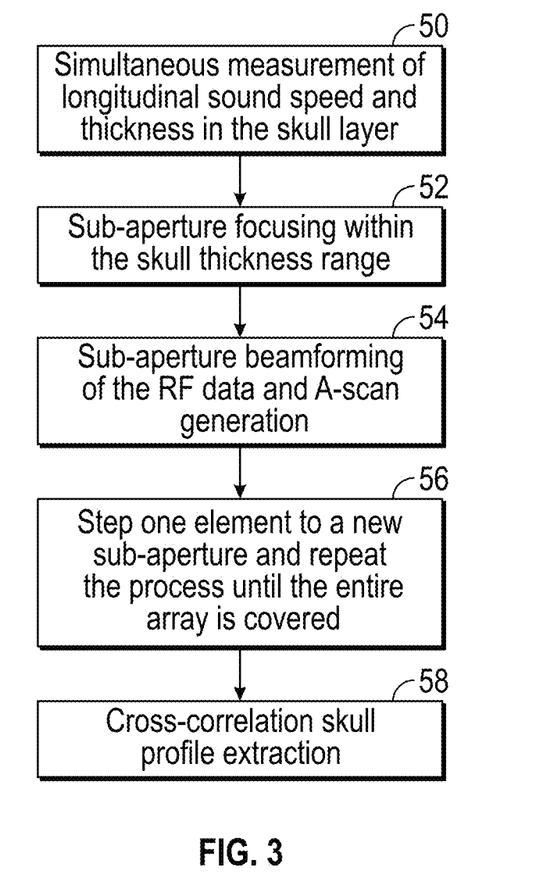
FIG. 3 is a flowchart of the one embodiment for skull profile extraction.

FIG. 2 illustrates the matrix of elements 44 of the probe 12. A higher or lower number of elements 44 could be used. FIG. 3 is a flowchart of the one embodiment for skull profile extraction.

Referring to FIGS. 2 and 3, in one embodiment, to extract the skull 36 profile via the same imaging matrix probe 12 prior to the main beamforming process, first the longitudinal sound speed in the skull layer 36 is measured, such as by using a simultaneous thickness/speed measurement technique in step 50. In step 52, a small sub-aperture 46 of the matrix probe elements 44 at a time is arranged to focus at about the skull layer's 36 thickness, e.g. ~1 cm distance from the probe's surface. In FIG. 2, the sub-aperture 46 comprises nine elements 44, but the number of elements could be higher or lower. Starting from one corner of the array, this small aperture 46 is moved in single element steps to the opposite corner of the matrix probe 12 in a raster scanning manner (or other pattern). The line in FIG. 2 shows one possible scanning path of the center element 44 of the nine-element aperture 46. At each step, multiple acquisitions of the RF signals are recorded, averaged and fed through standard nine-element beamforming and summation processes in step 54. The sub aperture 46 is then incremented along the path by one element in step 56. The profile of the skull layer in front of the matrix probe is then extracted by a cross-correlation algorithm in step 58.

2. Single-point Adaptive Focusing

Figure 4:
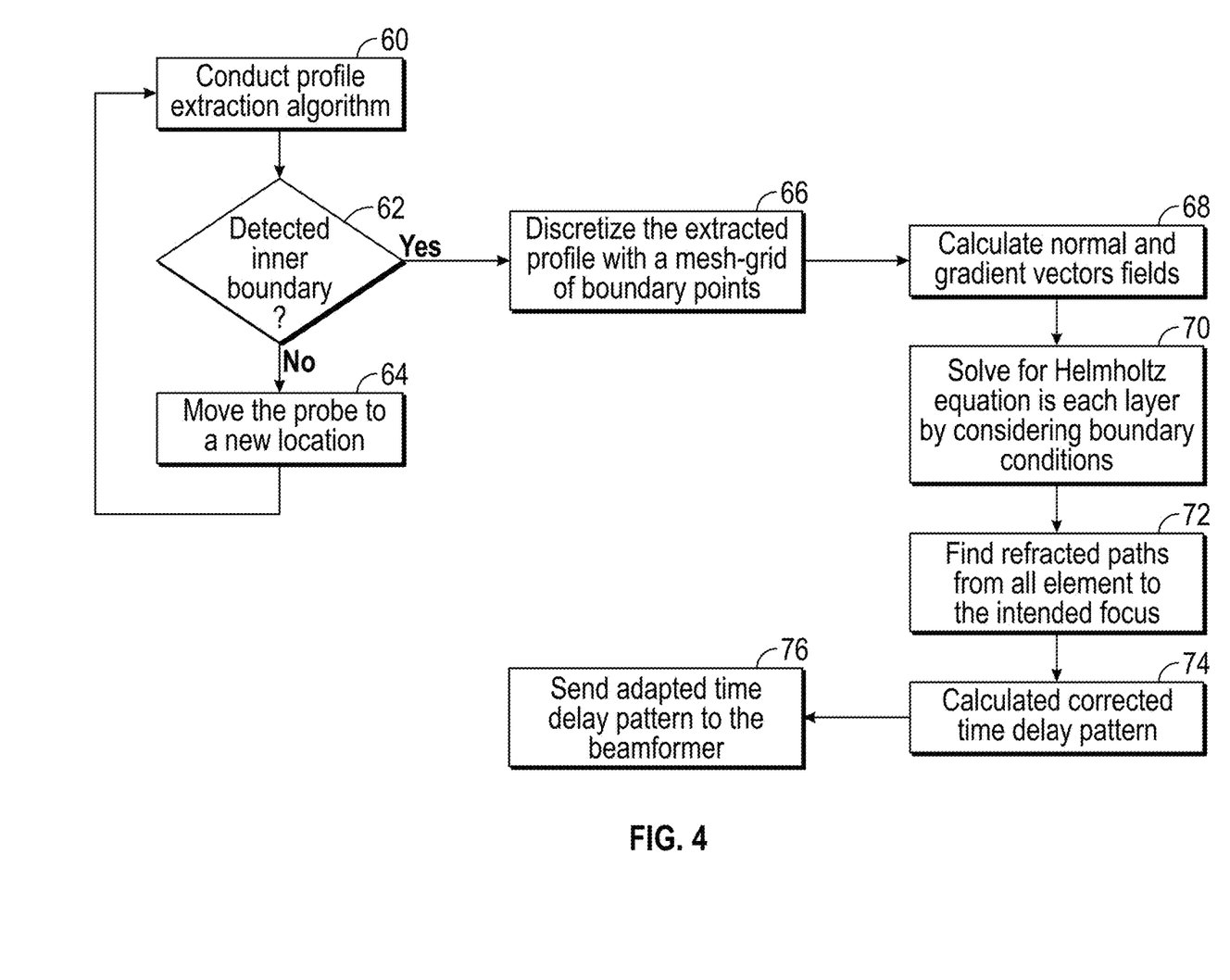
FIG. 4 is a flowchart of an example single-point adaptive focusing method.

The skull profile extraction algorithm comprised of steps 50-58 outputs the inner surface profile needed by the adaptive focusing algorithm. As the matrix probe 12 is placed in contact with the skull layer 36, the skull profile extraction algorithm is executed in its entirety in step 60. Step 62 is a check whether this execution went without errors and produced a valid skull profile or an error occurred. An error means the algorithm has failed to detect a valid skull profile due to poor contact between the probe and the skull, due to extremely rough inner surface of the skull, extreme porosity at this location, or for other reasons. In case of an error, step 64 directs moving the probe to a different location and repeating from step 60 until a valid skull profile is detected and check at step 64 switches the execution to step 66.

To implement the outlined beamforming method, a ray-tracing computer model has been developed to simulate acoustical beam patterns in the skull-brain propagation environment followed by calculation of the adapted timing patterns. This model incorporates the effects of phase aberration and attenuation by the acoustic barrier and by the rest of the propagation media (e.g. by the human skull and the brain tissue). Based on the measured variable thickness of the skull segment under the phased array and the acoustic impedance mismatch between skull and brain tissue, the refracted acoustic ray paths connecting active array elements with each intended focal area are numerically calculated through the computer model. For this, first the extracted skull profile is discretized with a mesh-grid of boundary points in step 66. The grid size is automatically chosen based on the thickness gradient of the extracted skull profile. In step 68, normal and gradient vectors are calculated over the inner boundary of the extracted skull layer at each grid point. The normal and gradient vectors fields are then output to the main body of the ray-tracing code.

To find physically possible refracted paths from each active array element to a desired focal point in step 72, the Helmholtz wave propagation equation:

$$\frac{1}{r^2}\frac{\partial}{\partial r}\left(r^2\frac{\partial \Phi}{\partial x}\right) + \frac{1}{r^2\sin\theta}\frac{\partial}{\partial \theta}\left(\sin\theta\frac{\partial \Phi}{\partial \theta}\right) + \frac{1}{r^2\sin^2\theta}\frac{\partial^2 \Phi}{\partial \varphi^2} + k^2\Phi(r,\theta,\varphi;\omega) = 0 \quad (1)$$

is solved numerically in each medium with appropriate boundary conditions in step 70. For this, the algorithm searches through the boundary points and picks the one at which all constraints are satisfied. In the proposed algorithm, there are three major constraints to be satisfied:

1. The normal vector at each grid point should be perpendicular to the norm of the communal plane of incident and refracted beams;
2. The intracranial sound pressure must be equal to the normal component of the stress just within the skull layer; the tangential stress in the skull must vanish, and the normal component of the velocity must be continuous;
3. Fermat's principle.

Figure 5:
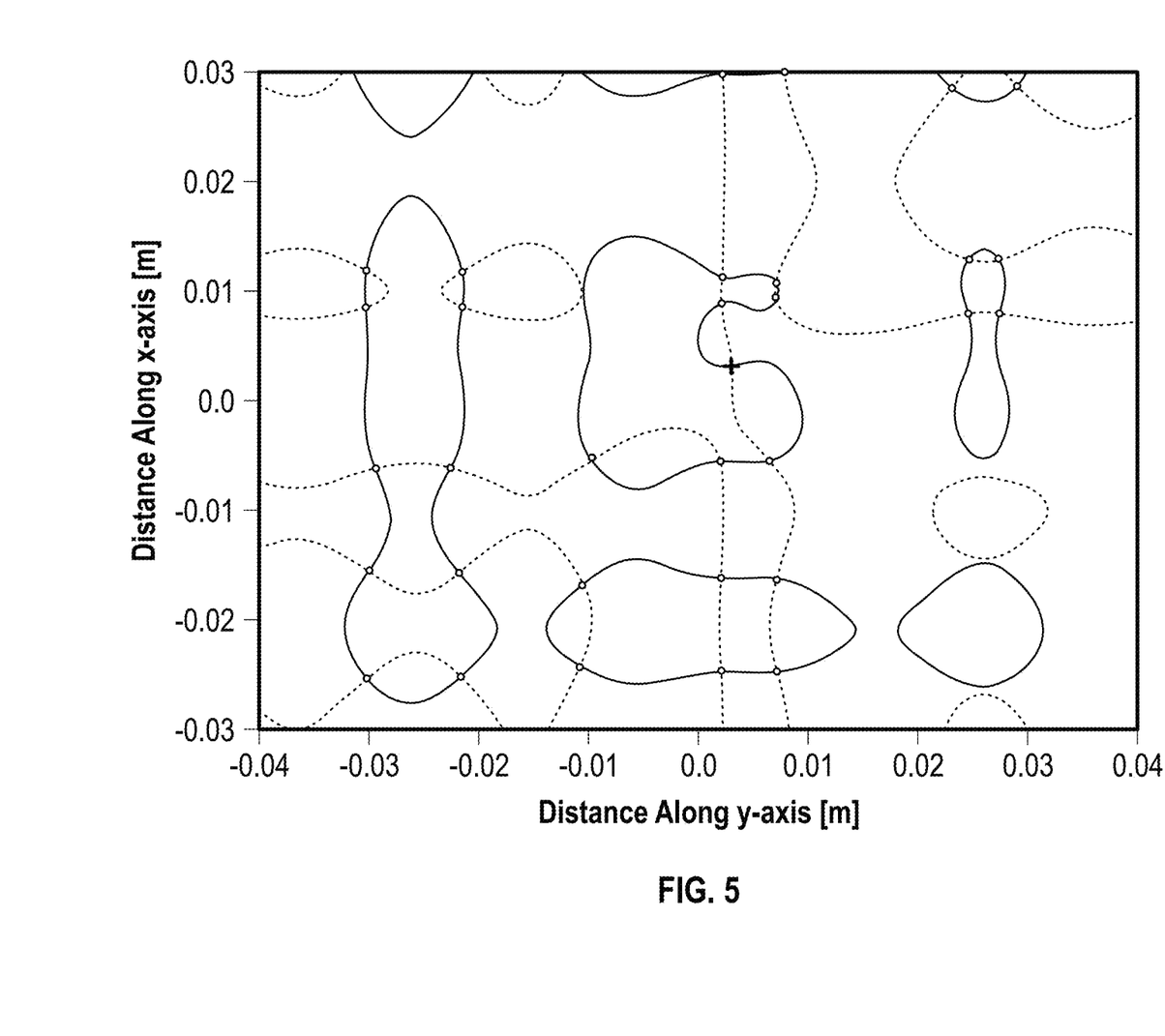
FIG. 5 shows example contour plots of the boundary points which satisfy the first two boundary conditions when seeking for the refracted path between one particular element of the matrix array and one particular intended focal point in a single-point adaptive focusing scenario.

In the computer model, first contour plots of the skull-brain boundary points which satisfy the first two boundary conditions are calculated. Example of such contour plots are shown in FIG. 5. The solid curves are contour-plots of the boundary points at which the first constraint is satisfied; and the dotted lines are contour-plots of the boundary points at which the second constraint is satisfied. The intersection points of the two plots satisfy both constraints. These points are identified by small black circles in FIG. 5. Among these selected points, the one that will correspond to the shortest refracted path between the selected array element and the intended focal point is selected based on the Fermat's principle. This point is shown by a small cross in FIG. 5. Therefore the ultrasound transmitted from the array element under consideration to the desired focal point in the brain will pass through this point on the skull-brain interface.

For optimum results, more points are interpolated in between the original grid points on highly undulating areas of the inner boundary; on the other hand, when the thickness profile has a smooth variation, some boundary points may be skipped. The above process is then repeated for all the active elements on the array to find all the refracted paths.

With the knowledge of these refracted paths for each single-point focusing scenario, in step 74 the model calculates the corrected time delay pattern for the array elements through $$\tau_{nm} = \frac{1}{c_0}\left[\sqrt{R_F^2 + \frac{d^2}{4}[(N-1)^2 + (M-1)^2] + [(N-1)\cos\phi + (M-1)\sin\phi]dR_F\cos|\Psi|} - \sqrt{R_F^2 + (n^2+m^2)d^2 - 2(n\cos\phi + m\sin\phi)dR_F\cos\Psi}\right] \quad (2)$$

where the index n denotes the element number along x-axis for $-(N-1)/2 \leq n \leq (N-1)/2$, N is the total number of elements in width of the array. The index m denotes the element number along the y-axis for $-(M-1)/2 \leq m \leq (M-1)/2$, M is the total number of elements in length of the array. $c_0$ is the compression wave sound speed in propagation medium and d is the array's pitch. The adapted time delay pattern is sent to the beamformer in step 76.

3. Transmission and Reception Modes Adaptive Beamforming and Final Image Generation The above single-point adaptive focusing method is used to create adapted timing patterns (focal rules) for the phased array elements in transmission mode. When a particular new focal rule is applied, the ultrasound beam produced by the transmitting aperture is directed towards the intended focal point behind the barrier. To optimally probe the entire target volume behind the barrier, multiple focal rules can be successively created to steer the acoustic beam at different directions and to focus at multiple points along each direction.

Figure 6:
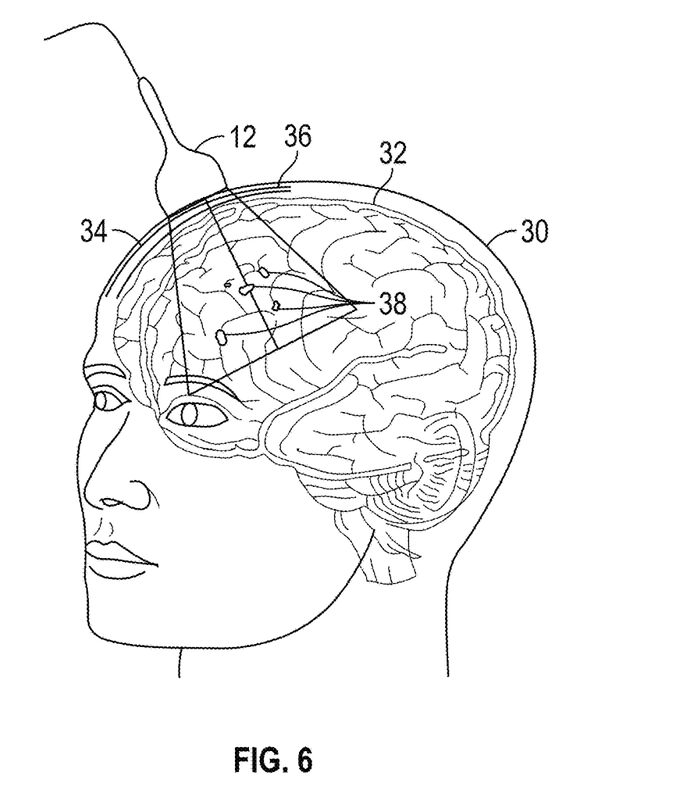
FIG. 6 shows a configurational imaging setup for the adaptive imaging method described herein.
Figure 7:
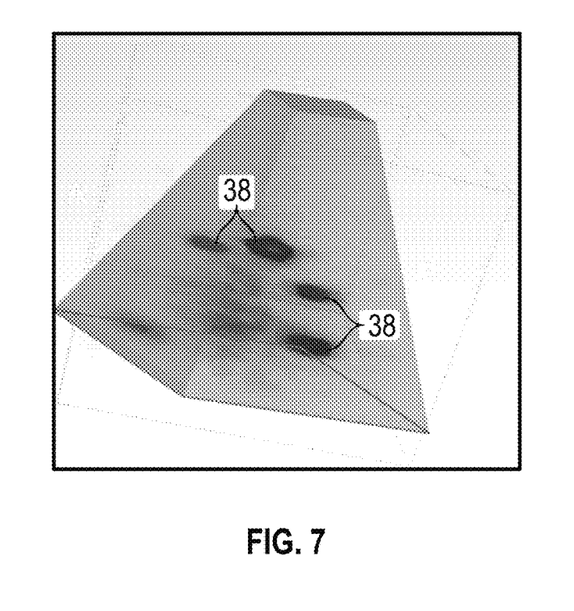
FIG. 7 shows a sample 3D sonogram showing high-impedance static objects through intact human skull.

For each particular focal rule in the transmission mode it is necessary to collect acoustic echoes from the propagation media. This is done by appropriately configuring a selected group of array elements 44 (receiving aperture) and represents the reception mode. The receiving aperture can be either the same as the transmitting aperture or different. In the reception mode, the explained above single-point adaptive focusing algorithm is employed, in a similar way to the transmission mode, but adapted for the passive dynamic focusing nature of this mode. The beamforming algorithm is used again to calculate and apply corrected timing patterns adapted to the geometry and acoustical properties of the barrier segment in contact with the array. The adapted timing patterns are then applied to the receiving elements on the array during dynamic focusing in reception mode right after each transmission shot. The adapted transmission and reception modes are then combined in the final image reconstruction process, which includes post-processing and filtration of received signals to assign an acoustical intensity value to each pixel and generate a final image (sonogram). An imaging setup is shown in FIG. 6. The final sonogram shows the targeted objects 38 in their correct positions (FIG. 7).

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. For example, it should be noted that although calculation and derivations are explained in case of a 2D probe for a 3D image generation, the disclosed here method can be applied to any other phased array geometry (e.g. 1D, 1.5D, conical, etc). The developed algorithm can be used for adaptive beamforming through any attenuative multilayered solid structure (acoustical barrier) having an acoustic impedance mismatch between the interfacing media. It can also be considered for large and synthetic aperture focusing.

What is claimed is:

1. A method for ultrasonic imaging a volume behind a barrier, the method including the steps of:
   a) placing an array of elements of a probe capable of transmitting and receiving ultrasound adjacent the barrier;
   b) estimating local thickness and sound speed in the barrier using the array of elements of the probe adjacent the barrier after said step a);
   c) defining a plurality of sub-apertures in the array of elements, each sub-aperture defined by a different subset of adjacent ones of the array of elements;
   d) collecting ultrasonic waveforms from each of the sub-apertures by focusing each sub-aperture approximately at the inner surface of the barrier based on the estimated thickness and estimated sound speed data obtained in said step b), the ultrasonic waveforms containing reflections from the front and inner surfaces of the barrier;
   e) combining the ultrasonic waveforms through each of the sub-aperture elements to generate a combined A-mode waveform for each of the sub-apertures;
   f) extracting a profile of an inner surface of the barrier adjacent the probe based upon the combined A-mode waveforms;
   g) calculating a correction based upon the profile of the inner surface, including discretizing the inner surface of the barrier into a grid of points in which spacing of the points is selected automatically based upon a local curvature on the inner surface of the barrier, calculating the correction for each element of the array of elements by tracing refracted acoustic rays between said each array element and an intended focal point through the barrier and the volume behind the barrier, wherein the corrections are in the form of modified time delays to achieve accurate single-point focusing, where the tracing of the refracted acoustic rays between each array element and the intended focal point through the grid of points on the inner surface of the barrier and the volume is accomplished by using the analytical solution to the Helmholtz wave propagation equation in homogeneous media to find the acoustic refracted paths in each of a plurality of mediums with appropriate boundary conditions, wherein the step of solving the Helmholtz wave propagation equation includes determining a first contour plot of a first subset of the grid of points at which a first boundary condition is satisfied, determining a second contour plot of a second subset of the grid of points at which a second boundary condition is satisfied, finding intersecting points of the first contour plot and the second contour plot wherein the intersecting points satisfy both the first boundary condition and the second boundary condition, and finding a selected point from the intersecting points as corresponding to a shortest path between the each array element and the intended focal point based upon Fermat's principle; and
   h) scanning the volume behind the barrier using beamforming based upon the correction to generate an image of the volume.

2. The method of claim 1 wherein an ultrasound transmitted from each of the array elements to the intended focal point in the volume will pass through a boundary point at which Fermat's principle and the first and second boundary conditions are satisfied.

3. The method of claim 2 further including a step of interpolating more points between the grid of points on highly undulating areas of the inner surface.

4. The method of claim 1 wherein said step h) is performed in both active mode and passive mode, wherein the active mode accurately focuses the acoustic field emitted by the probe and transmitted through the barrier at intended focal locations behind the barrier, and the passive mode accurately focuses the acoustic energy reflected from the media behind the barrier, passing through the barrier, and received by the probe and generates an image.

5. The method of claim 4 wherein the passive mode includes adjusting delays in received signals based upon the corrections.

6. The method of claim 4 wherein the passive mode includes corrections adapted for dynamic focusing.

7. The method of claim 4 further including the steps of applying corrected timing patterns adapted to geometry and acoustical properties of the barrier, applying the corrected timing patterns to receiving elements the array during dynamic focusing in reception mode, combining the active mode and passive mode in a final image reconstruction process.

8. The method of claim 1 further including a step of optimizing the beamforming of said step h) for side lobe suppression.

9. The method of claim 1 wherein the local thickness of the barrier is estimated in said step b) based upon the sound speed of the barrier determined in said step b).

10. The method of claim 1 wherein the barrier is a skull and the volume is brain tissue.

11. The method of claim 10 wherein said step h) is performed using the array of elements of the probe of said step a).

12. The method of claim 11 wherein the local thickness and sound speed in the barrier are estimated simultaneously in said step b).

13. An imaging system for providing ultrasonic imaging a volume behind a barrier comprising:
an ultrasonic phased array probe including an array of elements capable of transmitting and receiving ultrasound adjacent a barrier; and
a controller connected to the probe and configured to send instructions to the probe and to receive signals from the probe, the controller configured to estimate local thickness and sound speed in the barrier based upon signals from the probe, the controller configured to define a plurality of sub-apertures in the array of elements, each sub-aperture defined by a different sub-set of adjacent ones of the array of elements, the controller configured to collect ultrasonic waveforms from each of the sub-apertures by focusing each sub-aperture approximately at the inner surface of the barrier based on the estimated thickness and estimated sound speed data, the ultrasonic waveforms containing reflections from the front and inner surfaces of the barrier, the controller further configured to combine the ultrasonic waveforms through each of the sub-aperture elements to generate a combined A-mode waveform for each of the sub-apertures; the controller configured to extract a profile of an inner surface of the barrier adjacent the probe based upon the combined A-mode waveforms, the controller configured to calculate a correction based upon the profile of the inner surface, including discretizing the inner surface of the barrier into a grid of points in which spacing of the points is selected automatically based upon a local curvature on the inner surface of the barrier, calculating the correction for each element of the array of elements by tracing refracted acoustic rays between said each array element and an intended focal point through the barrier and the volume behind the barrier, wherein the corrections are in the form of modified time delays to achieve accurate single-point focusing, where the tracing of the refracted acoustic rays between each array element and the intended focal point through the grid of points on the inner surface of the barrier and the volume is accomplished by using the analytical solution to the Helmholtz wave propagation equation in homogeneous media to find the acoustic refracted paths in each of a plurality of mediums with appropriate boundary conditions, wherein solving the Helmholtz wave propagation equation includes determining a first contour plot of a first subset of the grid of points at which a first boundary condition is satisfied, determining a second contour plot of a second subset of the grid of points at which a second boundary condition is satisfied, finding intersecting points of the first contour plot and the second contour plot wherein the intersecting points satisfy both the first boundary condition and the second boundary condition, and finding a selected point from the intersecting points as corresponding to a shortest path between the each array element and the intended focal point based upon Fermat's principle, the controller configured to control the probe to scan the volume behind the barrier using beamforming based upon the correction to generate an image of the volume.

14. The imaging system of claim 13 wherein the controller is programmed to calculate the correction for each element in a transmission mode, the controller configured to calculate and apply correction in a receiving mode using a single-point adaptive focusing algorithm adapted for passive dynamic focusing.

* * * * *

UNITED STATES PATENT AND TRADEMARK OFFICE
CERTIFICATE OF CORRECTION

PATENT NO. : 10,330,782 B2  
APPLICATION NO. : 14/935999  
DATED : June 25, 2019  
INVENTOR(S) : Maev et al.

Page 1 of 1

It is certified that error appears in the above-identified patent and that said Letters Patent is hereby corrected as shown below:

In the Claims

In Claim 1, Column 7, Line 55; replace "the inner surface" with --an inner surface--

In Claim 1, Column 7, Line 58; replace "from the front and inner surfaces" with --from a front surface and the inner surface--

In Claim 1, Column 7, Line 63; replace "an inner surface" with --the inner surface--

In Claim 4, Column 8, Line 46; replace "focuses the acoustic energy" with --focuses acoustic energy--

In Claim 13, Column 9, Line 24; replace "the inner surface" with --an inner surface--

In Claim 13, Column 9, Line 26-27; replace "from the front and inner surfaces" with --from a front surface and the inner surface--

In Claim 13, Column 9, Line 32; replace "of an inner surface" with --of the inner surface--

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*